(12) United States Patent
Kitawaki et al.

(10) Patent No.: US 7,754,151 B2
(45) Date of Patent: Jul. 13, 2010

(54) LIQUID HOMOGENIZER AND ANALYZER EMPLOYING THE SAME

(75) Inventors: Fumihisa Kitawaki, Ehime (JP); Hirotaka Tanaka, Ehime (JP); Kenji Watanabe, Ehime (JP)

(73) Assignee: Panasonic Corporation, Osaka (JP)

( * ) Notice: Subject to any disclaimer, the term of this patent is extended or adjusted under 35 U.S.C. 154(b) by 319 days.

(21) Appl. No.: 11/910,513

(22) PCT Filed: Mar. 24, 2006

(86) PCT No.: PCT/JP2006/305956
§ 371 (c)(1),
(2), (4) Date: Oct. 2, 2007

(87) PCT Pub. No.: WO2006/106608
PCT Pub. Date: Oct. 12, 2006

(65) Prior Publication Data
US 2008/0292502 A1 Nov. 27, 2008

(30) Foreign Application Priority Data
Apr. 4, 2005 (JP) .............................. 2005-107658

(51) Int. Cl.
*G01N 9/30* (2006.01)
(52) U.S. Cl. .................. 422/72; 422/68.1; 422/99; 422/100; 436/45; 436/180
(58) Field of Classification Search ............ 422/50, 422/68.1, 72, 68, 1, 99, 100, 102, 104; 436/43, 436/45, 174, 178, 180; 366/134
See application file for complete search history.

(56) References Cited

U.S. PATENT DOCUMENTS 3,185,166 A 5/1965 Horton et al.
3,474,805 A 10/1969 Swartz et al.

(Continued)

FOREIGN PATENT DOCUMENTS

JP 7-191032 A 7/1995

(Continued)

OTHER PUBLICATIONS

International Search Report dated Jun. 20, 2006.

*Primary Examiner*—Jill Warden
*Assistant Examiner*—Sharon Pregler
(74) *Attorney, Agent, or Firm*—Pearne & Gordon LLP

(57) ABSTRACT

Herein disclosed is a liquid homogenizer for mixing two or more liquids, comprising: a rotator (1) rotatable around a rotation axis; at least two liquid-mixing chambers (6, 10) formed in the rotator, and being different from each other in distance from the rotation axis; and at least two channels (8) through which one of the liquid-mixing chambers is communicated with the other of the liquid-mixing chambers (6, 10), wherein the liquid-mixing chambers (6, 10) include an outer liquid-mixing chamber (10) and an inner liquid-mixing chamber (6) close to the rotation axis in comparison with the outer liquid-mixing chamber, when the rotator (1) is rotating around the rotation axis, the liquids are shifted by a centrifugal force to the outer liquid-mixing chamber from the inner liquid-mixing chamber through the channels (8), and agitated to be mixed by turbulent flows in the outer liquid-mixing chamber.

13 Claims, 12 Drawing Sheets

U.S. PATENT DOCUMENTS

| | | | |
|---|---|---|---|
| 5,876,187 A | 3/1999 | Afromowitz et al. | |
| 6,537,501 B1 | 3/2003 | Holl et al. | |
| 6,582,662 B1 * | 6/2003 | Kellogg et al. | 422/72 |

FOREIGN PATENT DOCUMENTS

| | | |
|---|---|---|
| JP | 10-505672 A | 6/1998 |
| JP | 2002-530786 A | 9/2002 |
| JP | 2003-028883 A | 1/2003 |
| JP | 2003-533681 A | 11/2003 |
| JP | 2003-533682 A | 11/2003 |
| JP | 2004-529312 A | 9/2004 |
| JP | 2004-294417 A | 10/2004 |
| JP | 2005-77397 A | 3/2005 |
| JP | 2005-114438 A | 4/2005 |
| WO | 98/53311 | 11/1998 |
| WO | 99/60397 | 11/1999 |
| WO | 00/79285 A2 | 12/2000 |
| WO | 01/87487 A2 | 11/2001 |

* cited by examiner (a)

(b)

(a)

(b)

(a)

(b)

(a)

(b)

LIQUID HOMOGENIZER AND ANALYZER EMPLOYING THE SAME

TECHNICAL FIELD

The present invention relates to a liquid homogenizer for mixing liquids using a centrifugal force generated by a rotational movement, and an analyzer employing the same.

BACKGROUND ART

Up until now, there has been widely used a conventional analyzer in the field of clinical examination, biochemical examination, and general experiment and research to analyze an ingredient in a liquid specimen reacted with a reagent which is arranged beforehand, the liquid specimen exemplified by a blood and a urine. Recently, the conventional analyzer of this kind has been constructed to be automatically operated so that a series of processes, that is, a process of absorbing and shifting the liquid specimen, a process of mixing the liquid specimen with the reagent, a process of measuring and analyzing the liquid specimen, a process of displaying a result of the analysis, and a process of recording the result, are automatically conducted with the simple placement of the liquid specimen, or a sample. This type of analyzer is generally adapted to shift the liquid specimen with a pressure, i.e., a positive pressure or a negative pressure generated by a pump. Meanwhile, there has also been proposed another conventional analyzer for analyzing a specimen, having a disc adapted to shift the specimen and the reagent by applying a centrifugal force generated by a rotation of the disc. This type of conventional analyzer utilizes a focusing technology and a tracking technology used in the optical disc device exemplified by a CD-ROM (compact disc read only memory) device are applied to the analyzer (see patent document 1). The analyzer for analyzing a liquid specimen with the disc shape is referred to as a disc analyzer.

FIG. 12 is a schematic view showing an example of the above-mentioned analyzer, where FIG. 12(a) is a cross sectional view and FIG. 12(b) is a perspective view. The same constitutional elements in these drawings will bear the same reference numerals and legends. As shown in the drawings, the device 200 has an appearance substantially the same as the conventional optical disc, that is, a disc having a center hole 203 formed at the center of the disc, the disc having four specimen inlet ports 201 formed to be positioned circumferentially around the center hole 203. The specimen inlet ports 201 are respectively communicated with four channels 202 formed in the above-mentioned disc. Each of the four channels 202 is formed radially from the center of the disc to the circumference and blocked at one end, and adapted to have a reagent for analyzing held in the middle thereof. The upper side of each of the channels 202 is permeable to light so that the reaction between the liquid specimen and the reagent in the channels can be optically measured. The method of analysis using this analyzer will now be described hereinafter. Firstly, a liquid specimen, such as a blood and a urine, is injected in the device 200 from the specimen inlet ports 201. The device 200 is then rotated by a rotation device, which results in the fact that the injected liquid specimen is urged, by the generated centrifugal force, to be shifted to the circumference from the center through the channels 202, with the liquid specimen being reacted with the liquid reagent. The ingredient analysis of the specimen is then conducted by means of detecting the liquid specimen or measuring the reaction with the above-mentioned focusing technology and the tracking technology. In this example, the specimen is shifted by the centrifugal force. However, the specimen may be shifted by capillary force, a siphon effect, and so on.

The analysis of the liquid specimen is required to be conducted with a process of diluting the liquid specimen, a process of introducing the reagent to the liquid specimen, a process of reacting the liquid specimen with the reagent, and a process of removing a reagent unreacted with the liquid specimen. In order for the processes to be conducted, a plurality of chambers are formed in the rotation device, where the processes are respectively conducted in the chambers. The chambers are formed to be communicated with each other through channels.

The liquid specimen is required to be evenly mixed in the above-mentioned processes. For example, the liquid specimen and a solvent are required to be evenly mixed in the process of diluting the liquid specimen. The liquid specimen and the reagent are required to be evenly mixed in the process of reacting.

In order to achieve a homogeneous mixture of the liquid material, a turbulent flow is required to be caused by the liquid material. As a method of generating the turbulent flow, a device such as a stirrer and VORTEX (trademark) is well known. In the method of using the stirrer, the turbulent flow is generated in such a way that a magnetically-charged stirrer bar is inserted in a container filled with materials to be mixed, and the stirrer bar is magnetically driven to be rotated by a magnet positioned outside of the container. In the method of using VORTEX (trademark), the turbulent flow is generated in such a way that the materials to be mixed are poured into a container such as a test tube, and then the bottom of the container is pressed to VORTEX (trademark) to ensure that the container is vibrated.

The analyzer which is required to have the function of rotating the disc has, however, such a problem that the apparatus becomes huge in size and complicated in constitution in the case that the apparatus has an additional function similar to the function of the above-mentioned stirrer or VORTEX (trademark).

Therefore, the method of mixing the liquids utilizing not the functions of the stirrer and VORTEX (trademark) but the shapes of the channels is under review. For example, there has been developed a device for mixing liquids having a winding channel as disclosed in patent document 2. The constitution of the device makes it possible to lengthen the traveling distance of the liquid. This leads to the fact that the device can lengthen the time to shift the liquid, which results in the mixed liquid or the mixture sufficiently diffused.

Patent document 1: International Publication Pamphlet No. 00/026677
Patent document 2: U.S. Pat. No. 6,582,662

DISCLOSURE OF THE INVENTION

Problems to be Solved by the Invention

The purpose of mixing and homogenizing two or more materials is to achieve highly reproducible reaction following the mixing and homogenizing, or to achieve highly reproducible detection by means of electrochemical or optical method for detecting amount of physical or chemical change caused by the reaction. This leads to the fact that it is necessary for the analyzer to additionally have a space for accommodating means, such as a reaction means and a detection means, along with the rotation device and the mixing channel. The analyzer has, however, such a problem that it is required to have a sufficient space to form the mixing channels of the rotation device, which results in the fact that it is troublesome for the analyzer to have such mixing channels due to the limitation in size, and that it is required to be constructed such that the liquids are mixed with small space and high efficiency.

It is, therefore, an object of the present invention to provide a liquid homogenizer which can evenly mix liquids with small space.

Means for Solving the Problems

In accordance with the present invention, there is provided a liquid homogenizer for mixing two or more liquids, comprising: a rotator rotatable around a rotation axis; at least two liquid-mixing chambers formed in the rotator, and being different from each other in distance from the rotation axis; and at least two channels through which one of the liquid-mixing chambers is communicated with the other of the liquid-mixing chambers, wherein the liquid-mixing chambers include an outer liquid-mixing chamber and an inner liquid-mixing chamber close to the rotation axis in comparison with the outer liquid-mixing chamber, when the rotator is rotating around the rotation axis, the liquids are shifted by a centrifugal force to the outer liquid-mixing chamber from the inner liquid-mixing chamber through the channels, and agitated to be mixed by turbulent flows in the outer liquid-mixing chamber.

The liquid homogenizer according to the present invention can inject the liquids through the plurality of channels to the chamber, where the injected liquids are collided with each other while causing a turbulent flow, which results in the liquids to be evenly mixed. This step is repeatedly conducted with the same number of times as the number of liquid-mixing chambers. This results in the fact that it is not necessary for the liquid homogenizer to have winding channels due to the fact that the liquids are not necessary to be mixed in the channels. Therefore, the analyzer thus constructed can evenly and efficiently mix the liquids with small space because of the fact that the analyzer is not required to have a large space to have the winding channels formed therein.

In accordance with the present invention, there is provided a liquid homogenizer, wherein the inner liquid-mixing chamber has emission ports to have the liquids emitted therethrough, the outer liquid-mixing chamber has inlet ports to have the liquids injected therethrough, the channels are respectively extended from the emission ports to the inlet ports, and the channels have folded parts being closer to the rotation axis than the emission ports of the inner liquid-mixing chamber.

The liquid homogenizer according to the present invention can temporarily hold a liquid in the proximity of the liquid-mixing chamber and the folded parts, which leads to the fact that the turbulent flow is certainly generated when the liquid is injected to the outer liquid-mixing chamber through the channels.

In accordance with the present invention, there is provided a liquid homogenizer, wherein said inner liquid-mixing chamber is defined by surfaces including a closest surface closest to said rotation axis of all said surfaces, and said folded parts of said channels extending from said inner liquid-mixing chamber are farther in comparison with said closest surface to said rotation axis.

The liquid homogenizer according to the present invention can have the liquid sequentially shifted between the liquid-mixing chambers with one rotation operation.

In accordance with the present invention, there is provided a liquid homogenizer, wherein said liquid-mixing chambers have air openings formed thereon, and said folded parts are formed away from said rotation axis with a predetermined distance, said predetermined distance being set so that said inner liquid-mixing chamber has a partial space having a volume substantially larger than air volume injected through said air openings when said rotator is rotating, said partial space being defined by said closest surface and another surface having a distance, from said rotation axis, equal to the distance between said rotation axis and said folded part.

The liquid homogenizer according to the present invention can prevent the liquid flow to be interrupted by air partly remained in the liquid-mixing chamber under the condition that the liquid is shifting, thereby resulting in the fact that the liquid homogenizer can have the liquid sequentially shifted between the plurality of liquid-mixing chambers. The liquid homogenizer according to this embodiment can be combined with the liquid homogenizer according to any other embodiments of this invention.

In accordance with the present invention, there is provided a liquid homogenizer, wherein said folded parts of said channels extended from each liquid-mixing chamber are formed to be equal in distances with each other from said rotation axis.

The liquid homogenizer according to the present invention can inject the divided liquids, the liquids divided by two more channels, to the outer liquid-mixing chamber with the same timing after the divided liquids passing through the respective folded parts with the same timing.

In accordance with the present invention, there is provided a liquid homogenizer, wherein said inlet ports of said outer liquid-mixing chamber are formed to be different in distance from said rotation axis with each other.

The liquid homogenizer according to the present invention can effectively collide the divided liquids passed through two or more channels by injecting one of the divided liquids from inner side of the liquid-mixing chamber and another of the divided liquids from outer side of the liquid-mixing chamber, which results in making the turbulent flow easier. This constitution is specially effective when the target liquid has low miscibility, low solubility, low reactivity, and high viscosity.

In accordance with the present invention, there is provided a liquid homogenizer, wherein said inner liquid-mixing chamber is larger in volume than that of said outer liquid-mixing chamber.

The liquid homogenizer according to the present invention can prevent the liquid flow to be interrupted by air partly remained in the liquid-mixing chamber under the condition that the liquid is shifting, thereby resulting in the fact that the liquid homogenizer can have the liquid sequentially shifted between the plurality of liquid-mixing chambers.

In accordance with the present invention, there is provided a liquid homogenizer, wherein said inner liquid-mixing chamber is defined by surfaces including a closest surface closest to said rotation axis of all said surfaces, and said folded parts of said channels extended from said inner liquid-mixing chamber are formed to be closer in comparison with said closest surface to said rotation axis.

The liquid homogenizer according to the present invention can have the liquid shifted not only by the centrifugal force but also by a capillary action. Therefore, the liquid homogenizer can homogenize the liquid with the repetition of rotating and halting the rotator. This stems from the fact that the liquid is urged to be shifted, by the centrifugal force, and stopped short of the folded part under the condition that the rotator is rotated. The liquid is then shifted again through the channel to the position short of the outer liquid-mixing chamber by the capillary action under the condition that the rotator is halted. The liquid is then injected to the outer liquid-mixing chamber by the centrifugal force when the rotator is again rotated. Moreover, the liquid homogenizer according to the present invention can have high flexibility in construction.

In accordance with the present invention, there is provided a liquid homogenizer, wherein said folded parts of said channels extended from each liquid-mixing chamber are formed to be different in distance to said rotation axis.

The liquid homogenizer according to the present invention can inject the liquids with the timing different from each other, which results in the fact that the liquids are effectively collided with each other to ensure that the turbulent flow is certainly caused. Therefore, the liquids are easily homogenized.

In accordance with the present invention, there is provided a liquid homogenizer, wherein said rotator is operated to be repetitively rotated and halted.

The liquid homogenizer according to the present invention can have high flexibility in construction.

In accordance with the present invention, there is provided a liquid homogenizer, wherein said inlet ports of said liquid-mixing chambers are formed to be upper in comparison with said emission ports in a thickness direction.

The liquid homogenizer according to the present invention can effectively utilize the space under the condition that the space is utilized in the thickness direction. For example, the channel extended from the inner liquid-mixing chamber is formed at the upper side portion with respect to the thickness direction, while the channel extended to the outer liquid-mixing chamber is formed at the lower side portion with respect to the thickness direction. This makes it possible for the people to design the constitutional elements without caring about the limitation of the space and without having the constitutional elements interfered with each other in the case that two or more channels and two or more liquid-mixing chambers are necessary to be formed, or in the case that the liquid homogenizer is required to have additional constitutional elements for additional functions.

In accordance with the present invention, there is provided an analyzer for analyzing a liquid specimen, comprising: a rotator; and two or more chambers and channels formed in said rotator, wherein said liquid specimen is urged to be shifted to one of said chambers by a centrifugal force generated by a rotation of said rotator through said channels, the liquid specimen being analyzed in the chamber, and further comprising the liquid homogenizer as set forth in any one of claims 1 to 11 for mixing two or more liquids, wherein said rotator, said channels, and said liquid-mixing chambers are at least partly formed by the rotator, the channels, and the liquid-mixing chambers of said liquid homogenizer.

The analyzer according to the present invention can inject the liquids through the plurality of channels to the chamber, where the injected liquids are collided with each other while causing a turbulent flow. This step is repeatedly conducted by the liquid homogenizer employed by the analyzer with the same number of times as the number of liquid-mixing chambers. This results in the fact that it is not necessary for the analyzer to have winding channels due to the fact that the liquids are not necessary to be mixed in the channels. Therefore, it is not necessary for the analyzer to have winding channels and have a large space to have the winding channels formed therein. The analyzer thus constructed can evenly and efficiently mix the liquids with small space, and that the measurement can be conducted with high repeatability, by means of electrochemical or optical method for detecting reaction or amount of physical or chemical change caused by the reaction. The analyzer according to the present invention may have a liquid-mixing chamber formed as a reaction chamber so that the liquid specimen and a reagent are reacted therein. The analyzer according to the present invention may have a liquid-mixing chamber formed as a pretreatment chamber so that the liquid specimen is pretreated therein.

Advantageous Effect of the Invention

The liquid homogenizer according to the present invention is adapted to inject the liquids through the plurality of channels to the plurality of chambers, where the injected liquids are collided with each other while causing a turbulent flow, which results in the liquids to be evenly mixed. Therefore, the liquid homogenizer is not required to have winding channels and have a large space to have the winding channels formed therein due to the fact that the liquids are not necessary to be mixed in the channels. The liquid homogenizer is available for an analyzer which can evenly and efficiently mix the liquids with small space, and that the measurement can be conducted with high repeatability, by means of electrochemical or optical method for detecting reaction or amount of physical or chemical change caused by the reaction.

BRIEF DESCRIPTION OF THE DRAWINGS

FIG. 2(a) shows the first base substrate, FIG. 2(b) shows the second base substrate, and FIG. 2(c) shows the third base substrate;

FIG. 4(a) is a sectional view of the second base substrate before portions thereof are cut away, and FIG. 4(b) is a sectional view of the second base substrate after the portions are cut away;

FIG. 7(a) shows the first base substrate, FIG. 7(b) shows the second base substrate, and FIG. 7(c) shows the third base substrate;

FIG. 8(a) shows the positional relationship between the folded part and the liquid-mixing chamber of the liquid homogenizer shown in FIG. 1, and FIG. 8(b) shows the positional relationship between the folded part and the liquid-mixing chamber of the liquid homogenizer shown in FIG. 6;

FIG. 10(a) is the overall view of the liquid homogenizer, and FIG. 10(b) is the partial enlarged view of FIG. 10(a);

FIG. 11(a) is the overall view of the liquid homogenizer, and FIG. 11(b) is the partial enlarged view of FIG. 11(a); FIG. 11(a) is a sectional view of the rotation device, and FIG. 12(b) is a perspective view of the rotation device.

DESCRIPTION OF THE REFERENCE NUMERALS

Figure 1:
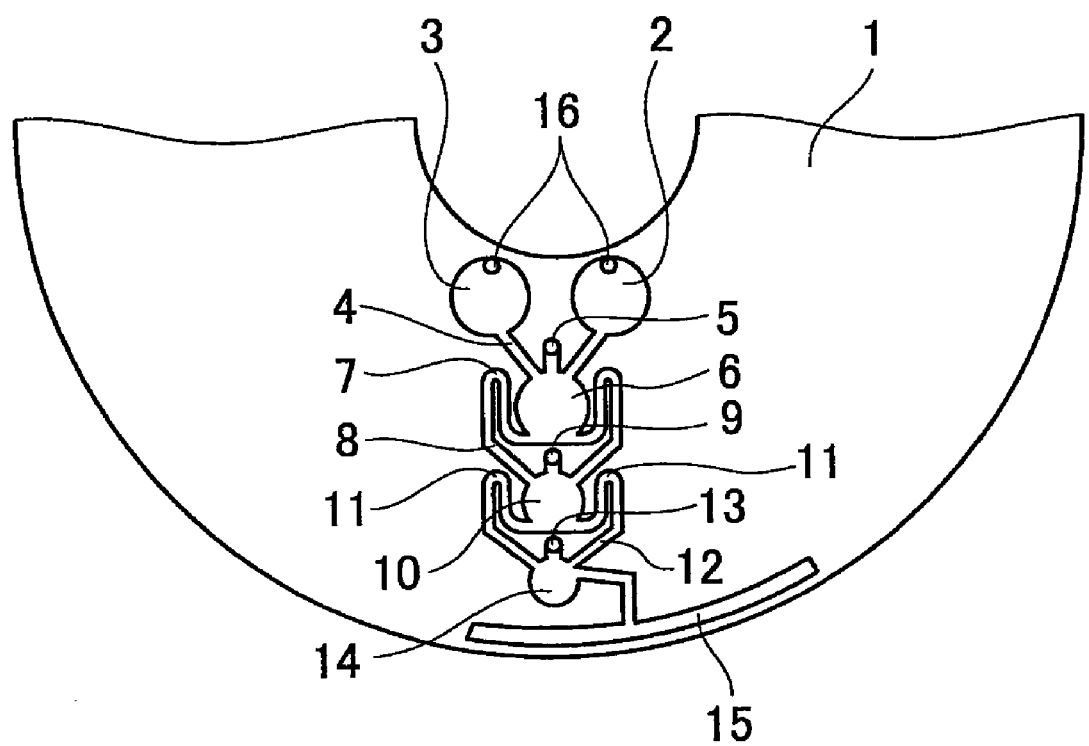
FIG. 1 is a plan view showing the liquid homogenizer according to the first example of the present invention.

1: rotator
2: specimen chamber
3: specimen chamber
4: straight channel
5: air opening
6: first liquid-mixing chamber
7: folded part (bending part)
8: channel
9: air opening
10: second liquid-mixing chamber
11: folded part (bending part)
12: channel
13: air opening
14: third liquid-mixing chamber
15: overflow chamber
16: specimen inlet port
21: release paper
22: adhesive layer
32: second base substrate
24: adhesive layer
25: release paper
31: first base substrate (cover member)
33: third base substrate (rotating substrate) (basal member)
50: rotator
51: first chamber
52: second chamber
53: third chamber
54: fourth chamber
55: fifth chamber
56: sixth chamber
60: specimen inlet port
61-66: air opening
71-75: inverted U-shape channel
81: first base substrate
82: second base substrate
83: third base substrate
101: rotator
102: specimen chamber
103: specimen chamber
104: straight channel
105: air opening
106: first liquid-mixing chamber
107: folded part (bending part)
108: channel
109: air opening
110: second liquid-mixing chamber
111: folded part (bending part)
112: channel
113: air opening
114: third liquid-mixing chamber
115: overflow chamber
116: specimen inlet port
200: device
201: specimen inlet port
202: channel
203: center hole

DESCRIPTION OF THE PREFERRED EMBODIMENTS

The embodiments of the liquid homogenizer according to the present invention will now be described in detail in accordance with examples and accompanying drawings.

Embodiment

The liquid homogenizer according to one embodiment of this invention comprises a rotator rotating around a predetermined rotation axis, a plurality of liquid-mixing chambers formed in the rotator and different in distance from the rotation axis with each other, and a plurality of channels respectively extending from and held in fluid communication with the liquid-mixing chambers. Each of the liquid-mixing chambers is communicated through two or more channels with another liquid-mixing chamber.

The liquid homogenizer according to this embodiment is constructed in such a way that the rotator has a combination of basic parts formed therein, the basic part being formed by liquid-mixing chambers communicated with each other through two or more channels. The liquid homogenizer can be formed by a plurality of base substrates, such as two or three base substrates, layered with each other. In the case that the rotator is formed by two base substrates layered with each other, the rotator is constituted by a base substrate with the above-mentioned basic parts formed therein and another base substrate without the basic parts formed therein, or constituted by a base substrate with the liquid-mixing chamber formed therein and another base substrate with the above-mentioned basic parts formed therein. In the case that the rotator is formed by three base substrates layered with each other, the rotator is constituted by a base substrate, as a middle layer, with the basic parts having a set of liquid-mixing chamber and channel formed therein, the base substrate sandwiched between two other base substrates attached thereto. One of the two other base substrates may only have a liquid-mixing chamber formed therein. In either case, it is necessary that the channels and the liquid-mixing chambers are defined by the rotator having a disc shape, and communicated with an air opening to ensure that the liquid flows therethrough smoothly.

The basic part according to the embodiment of this invention has two or more liquid-mixing chambers held in fluid communication with each other through two or more channels. The liquid injected in the basic part is urged to be shifted in the direction toward the circumference from the rotation axis (hereinafter simply referred to as an outward direction or an outer side) by centrifugal force generated by the rotation of the rotator. Resulting from the existence of the two or more channels formed between two liquid-mixing chambers, the liquid emitted from the inner liquid-mixing chamber is divided into two or more parts to be shifted along each of the two channels, and merged in one liquid in the outer liquid-mixing chamber. As described above, the basic part according to the embodiment of the invention has a function to homogenize the target liquid, the function being achieved by the process of dividing the liquid into two or more parts and then merging into one liquid to cause turbulent flow under the condition that the rotator is rotated.

Therefore, it would be preferable to increase the number of channels formed between two or more liquid-mixing chambers in terms of generating the turbulent flow. On the other hand, the constitution of the basic part becomes more complicated as the number of the channels is increased. The number of channels, therefore, should be determined suitably in accordance with the properties of the target liquid to be homogenized. The number of channels is, for example, determined in accordance with miscibility, solubility, reactivity, and viscosity of the target liquid. Specifically, the number of the channels can be small under the condition that the liquid has high miscibility, high solubility, high reactivity, and low viscosity, which leads to the fact that the number is preferable to be set at the numeral "2" to achieve the advantageous effect with simple constitution. On the other hand, the number of channels is preferable to be larger as long as the rotator can have enough space to form the channels under the condition that the liquid has immiscibility, low solubility, low reactivity, and high viscosity.

The number of two or more chambers communicated with each other through two or more channels according to the embodiment of the invention is preferable to be larger in terms of homogenizing the liquid. However, the constitution of the basic part becomes more complicated as the number of the liquid-mixing chambers is increased. This results in the fact that the number of the liquid-mixing chambers should be determined suitably in accordance with the properties of the target liquid to be homogenized together with the limitation of the space to form the liquid-mixing chambers. The number of liquid-mixing chambers is, for example, determined in accordance with the miscibility, solubility, reactivity, and viscosity of the target liquid. Specifically, the number of the channels can be small under the condition that the liquid has high miscibility, high solubility, and high reactivity, which leads to the fact that the number is preferable to be set at the numeral "2" due to the space to form the liquid-mixing chambers. On the other hand, the number of the liquid-mixing chambers is preferable to be larger as long as the rotator can have enough space to form the liquid-mixing chambers under the condition that the liquid has immiscibility, low solubility, low reactivity, and high viscosity.

Each of the channels according to the embodiment of this invention formed between two liquid-mixing chambers is, for example, extended from an emission port of the inner liquid-mixing chamber, where the liquid is emitted therethrough, to the predetermined inner side of the rotator, and then extended to the part which is outer side compared to the emission port of the inner liquid-mixing chamber, and to the inlet port of the outer liquid-mixing chamber through which the liquid is injected in the outer liquid-mixing chamber. Here, it is important that each of the channels has folded part which is extended toward the inner direction. In the case that the channel is formed without having a folded part extending toward the inner direction, the liquid is urged, by the centrifugal force generated by the rotation of the rotator, to pass through the liquid-mixing chamber without being accumulated in the liquid-mixing chamber. This results in the impossibility of sufficiently homogenizing the liquid due to the absence of the turbulent flow.

It is therefore necessary to hold, at least briefly, the liquid in the liquid-mixing chamber to ensure that the turbulent flow is generated. The channel according to the embodiment of the invention can prevent the liquid to be shifted to the following liquid-mixing chamber until the inner liquid-mixing chamber is filled with the liquid due to the fact that the channel is formed with the folded part extending toward the inner direction, which makes it possible to have the liquid temporarily held in the liquid-mixing chamber.

According to one embodiment of the invention, the liquid homogenizer is adapted to homogenize the liquid by having the liquid shifted between a plurality of liquid-mixing chambers with the one rotation operation of rotating the rotator to only once exert the centrifugal force to the liquid. In other words, the liquid homogenizer is adapted to repeat the process of sequentially dividing and merging liquid while the liquid is shifted between the plurality of chambers under the condition that the liquid is urged to be shifted by the centrifugal force exerted once by the rotation of the rotator. It is therefore necessary for the liquid homogenizer to be constructed so that the liquid sequentially flows between the plurality of liquid-mixing chambers with the one rotation operation.

In this embodiment, the channel is formed so that the folded part is positioned outer side compared to the portion of the surface of the inner liquid-mixing chamber, the portion positioned at the most inward side, where the channel is communicated with the inner liquid-mixing chamber. This constitution is aimed to achieve the sequential shift of the liquid between the plurality of liquid-mixing chambers with one rotation operation.

In addition, the folded part may be positioned apart from the rotation axis with a predetermined distance to ensure that the liquid is sequentially divided and merged repetitively when the liquid is shifted between the liquid-mixing chambers, the liquid shifted with the one rotation operation for once exerting the centrifugal force only once to the liquid. Here, the predetermined distance is preferred to be set such that the volume of partial space in the inner liquid-mixing chamber is substantially larger than the volume of the air injected through the air opening while the rotator is rotating, in which the partial space is defined by the side surface positioned most inward of the inner liquid-mixing chamber and a surface having a distance, from the rotation axis, equal to the distance between the rotation axis and the folded part.

The liquid homogenizer according to the embodiment of the invention can prevent the liquid flow to be interrupted by air partly remained in the liquid-mixing chamber under the condition that the liquid is shifting, thereby resulting in the fact that the liquid homogenizer can have the liquid sequentially shifted between the plurality of liquid-mixing chambers. The liquid homogenizer according to this invention may be constructed such that at least some portion of the liquid homogenizer according to this embodiment is combined with at least some portion of the liquid homogenizer according to any other embodiments. The volume of the air injected through the air opening while the rotator is rotating can be calculated in accordance with the conditions of the air opening, the conditions exemplified by a shape and a size. A volume of a partial space in the liquid-mixing chamber defined by the side surface positioned most inward and another surface having a distance, from the rotation axis, equal to the distance between the rotation axis and the folded part may be determined so that the liquid-mixing chamber can retain the liquid without the flow of the liquid being interrupted by the air injected in the liquid-mixing chamber while the rotator is rotating. In a precise sense, it is preferable that the volume be determined according to the characteristics of the liquid. For example, the volume can be slightly smaller than the volume of the injected air under the condition that the liquid has high viscosity and high affinity for the air.

In the process of sequentially shifting the liquids between the plurality of liquid-mixing chambers, the timing of injecting the liquids in each of the liquid-mixing chambers is important to merge the liquids. The liquids are injected to each of the liquid-mixing chambers through the two or more channels. In this case, the timing of injecting, at each of the liquid-mixing chambers, the liquids through each of the channels is required to be synchronized with each other. This stems from the fact that degree of collision between the divided liquids is reduced under the condition that there is time difference between the timing of injections, which results in difficulty in generating the turbulent flow. Therefore, the liquid homogenizer according to the embodiment of the invention is constructed such that the folded parts of respective channels, the channels extended from the inner liquid-mixing chamber, are placed with the distances equal to each other from the rotation axis, ensuring that the liquid is sequentially shifted between the liquid-mixing chambers by one rotation operation. This makes it possible for the divided liquids, divided by two or more channels, to respectively pass through the folded parts with the same timing, and injected in the liquid-mixing chamber with the same timing.

In the embodiment of this invention, positions of ports to communicate the channels with the liquid-mixing chambers are not limited. However, it is preferable that the relative position of the inlet port and the emission port is set so that the inlet port is positioned inner side compared to the emission port.

According to another embodiment of the invention, two or more inlet ports, for injecting the liquids through the channels, formed on the same outer liquid-mixing chamber may be positioned so that one of the inlet ports is positioned outer side compared to other inlet ports. This makes it possible to effectively collide the divided liquids passed through two or more channels by injecting one of the divided liquids from inner side of the liquid-mixing chamber and another of the divided liquids from outer side of the liquid-mixing chamber, which results in making the turbulent flow easier. This constitution is especially effective when the target liquid has low miscibility, low solubility, low reactivity, and high viscosity.

There has been described about the fact that the number of inlet ports and emission ports, formed on each liquid-mixing chamber, are respectively equal to the numbers of channels to have the liquid flowed into the liquid-mixing chamber and to have the liquid emitted out from the liquid-mixing chamber. However, it is within the scope of the invention that the number of channels may be more or less than the number of the respective inlet and emission ports under the condition that the liquid homogenizer has channels merged or diverged at the middle of the liquid-mixing chambers, as long as the rotator has enough space to form the channels. In this case, the plurality of channels are formed to be merged or diverged.

The liquid homogenizer according to another embodiment of the invention, which can have the liquid sequentially divided and merged repeatedly when the liquid is shifted between the liquid-mixing chambers with the one rotation operation for only once exerting the centrifugal force to the liquid, may have an inner liquid-mixing chamber having a volume larger than the volume of the outer liquid-mixing chamber. In other words, the liquid homogenizer can prevent the liquid flow to be interrupted by air partly remained in the liquid-mixing chamber when the liquid is shifting, under the condition that the inner liquid-mixing chamber is formed to have a volume larger than that of the outer liquid-mixing chamber. This makes it possible to sequentially shift the liquid in consequence. The liquid homogenizer according to this invention may be constructed such that at least some portion of the liquid homogenizer according to this embodiment is combined with at least some portion of the liquid homogenizer according to any other embodiments.

The liquid homogenizer according to another embodiment of the invention is constructed such that the rotation operation and halting operation are repetitively carried out to the rotator to ensure the liquid being shifted between the plurality of liquid-mixing chambers, which results in the liquid homogenized. In this case, it is important that the liquid is temporarily and completely held by the liquid-mixing chamber. The channel is, therefore, formed so that the folded part is positioned inner side compared to the side surface positioned most inward of the inner liquid-mixing chamber where the inner liquid-mixing chamber is communicated with other liquid-mixing chamber through the channel. The liquid held in the channel can be shifted not only by the centrifugal force but also by a capillary action. The liquid is urged to be shifted, by the centrifugal force, and stopped short of the folded part under the condition that the rotator is rotated. The liquid is then shifted again through the channel to the position short of the following liquid-mixing chamber by the capillary action under the condition that the rotator is halted. The liquid is then injected to the following liquid-mixing chamber by the centrifugal force when the rotator is again rotated.

The fact that the liquid is temporarily and completely held short of the folded part leads to the fact that the liquid homogenizer according to this invention can have high flexibility in designing. In other words, the divided liquids passing through respective two or more channels can temporarily be held completely in the liquid-mixing chamber and the channels short of the folded parts, which results in the fact that the timing of the liquids to be injected to the liquid-mixing chamber through two or more channels are not necessary to be synchronized with each other. Moreover, the collision between the divided liquids is caused more effectively in the case that the timing is not synchronized, which makes it possible to easily generate the turbulent flow, and facilitate the homogenization. In this case, the folded parts of two or more channels are not required to be positioned on the same imaginary surface, the imaginary surface positioned such that all points on the imaginary surface are positioned to be the same distance from the rotation axis. It is more preferable that the folded parts are positioned to be different in distance from the rotation axis, which makes it possible for the divided liquids to be injected in the liquid-mixing chamber with the timing deliberately different from each other.

The liquid homogenizer according to the embodiment of the invention can effectively utilize the space under the condition that the space is utilized in the thickness direction. For example, the channel extended from the inner liquid-mixing chamber is formed at the upper side portion in the thickness direction, while the channel extended to the outer liquid-mixing chamber is formed at the lower side portion in the thickness direction. This makes it possible for the people to design the constitutional elements without caring about the limitation of the space and without having the constitutional elements interfered with each other even if two or more channels and two or more liquid-mixing chambers are necessary to be formed, or even if the liquid homogenizer is required to have additional constitutional elements for additional functions.

In the case of constituting the rotator of this type with three layers will now be described. The upper layer among the three layers has a channel extended from the inner liquid-mixing chamber formed therein, and the lower layer has a channel extended to the outer liquid-mixing chamber formed therein. The channels in the upper layer and in the lower layer are formed to be extended to the middle layer so that the channels are communicated with each other.

The liquid homogenizer according to the embodiments of the invention is preferable to have an air opening provided to ensure the liquid-mixing chamber communicate with the external air therethrough. This makes it possible for the liquid homogenizer to have the liquid shifted smoothly.

The liquid homogenizer according to the embodiments of the invention is preferable to have an overflow chamber. The overflow chamber is adapted to receive the liquid mixed in and emitted from the liquid-mixing chamber, and to prevent the liquid from leaking from the liquid homogenizer. The overflow chamber may be adapted to determine the quantity of the liquid mixed in and emitted from the liquid-mixing chamber.

The liquid to be mixed by the liquid homogenizer according to the embodiments of this invention is exemplified by, but not limited to, a liquid specimen, a reagent, and a diluted solvent. The liquid specimen is exemplified by, but not limited to, a living specimen such as a blood or a urine. The diluted solvent is exemplified by a water, an organic solvent, and a buffer fluid. The buffer fluid is exemplified by a phosphate buffer, a tris buffer, and a carbonate buffer. The reagent is chosen in accordance with the type of the reaction exemplified by an enzyme reaction, an antigen-antibody reaction, a reaction with a receptor, detection reaction for a nucleic acid, and a cell destruction reaction. The reagent can be constituted by any solution as long as the solution contains a material reactive with another material in the specimen. This solution is constituted by a solvent such as a water, an organic solvent, and a buffer fluid. This buffer fluid is exemplified by a phosphate buffer, a tris buffer, and a carbonate buffer. The material reactive with another material in the specimen is exemplified by an enzyme, an antigen, an antibody, a receptor, a nucleic acid, an inorganic salt, and a surface active agent. In the case of the enzyme reaction, the material reactive with another material in the specimen is exemplified by an enzyme such as a glucose oxidase. In the case of the antigen-antibody reaction, the material reactive with another material in the specimen is exemplified by an antigen having a specific reaction with an antibody, such as HCV antibody and HIV antibody, in the specimen. In another case of the antigen-antibody reaction, the material reactive with another material in the specimen is exemplified by an antibody, such as a polyclonal antibody, a monoclonal antibody, a chimeric antibody, an Fab antibody, an F(ab)2 antibody, and an Fv antibody, having a specific reaction with an antigen in the specimen. In the case of the reaction with a receptor, the material reactive with another material in the specimen is exemplified by a receptor having a specific reaction with a physiologic active substance, such as a steroid, a hormone (a peptide hormone or the like), a vitamin, a growth factor, a cytokine, and a catecholamine, in the specimen. In the case of the detection reaction for a nucleic acid, the material reactive with another material in the specimen is exemplified by a DNA and an RNA. In the case of the cell destruction reaction, the material reactive with another material in the specimen is exemplified by an inorganic salt and a surface active agent. Here, the inorganic salt is adapted to promote the cell destruction with the contraction and dilation of the cell by varying an osmotic pressure between inside and outside of the cell. The surface active agent is adapted to promote the cell destruction by having a cell constituent, such as a protein and a phosphatide, lose the balance between hydrophilicity and hydrophobicity. The inorganic salt is exemplified by a sodium chloride, a potassium chloride, a sodium fluoride, a sodium thiocyanate, and a potassium thiocyanate. The surface active agent is exemplified by a sucrose monolaurate, a sodium oleate, and a sodium deoxycholate (SDS).

The liquid homogenizer according to the embodiments of this invention may have a living specimen initially in a dry state when the living specimen is used. For example, the liquid homogenizer is constructed such that the liquid specimen is coated and supported in a dry state on the base substrate before the base substrate is attached with another base substrate.

The liquid homogenizer is preferred, but not limited, to have a disc shape as described in this embodiment. Here, the liquid homogenizer may have any kinds of shape, such as a cartridge shape and a chip shape, as long as the shape is suitable to form the rotator.

Examples of the liquid homogenizer and the analyzer employing the liquid homogenizer according to the present invention, along with the comparative example of the liquid homogenizer, will be described in detail. Needless to say, the scope of the present invention is no way limited by the following examples.

FIRST EXAMPLE

Figure 2:
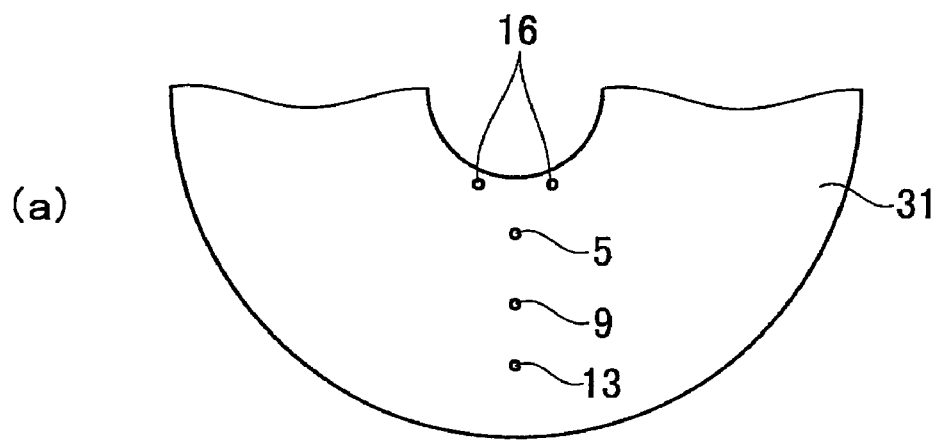
FIG. 2 is an exploded plan view showing the liquid homogenizer shown in FIG. 1, where
Figure 2:
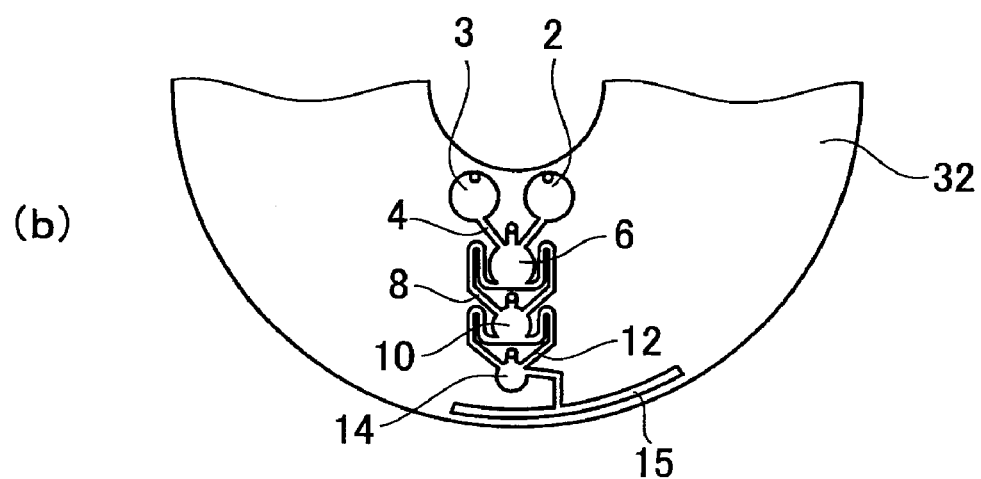
Figure 2:
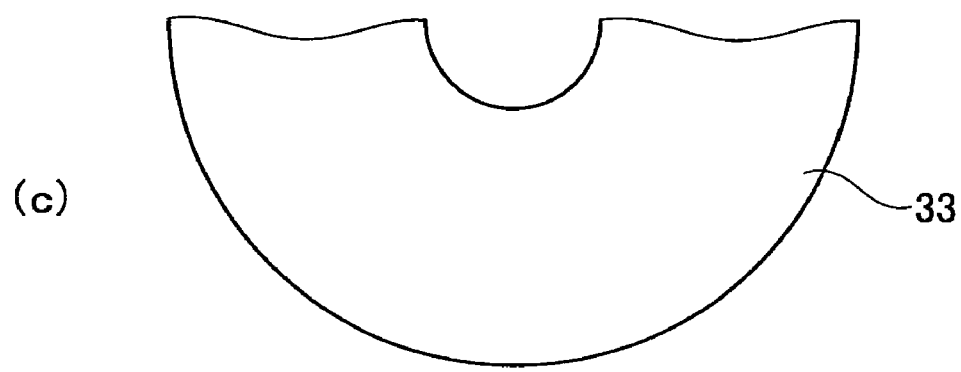
Figure 3:
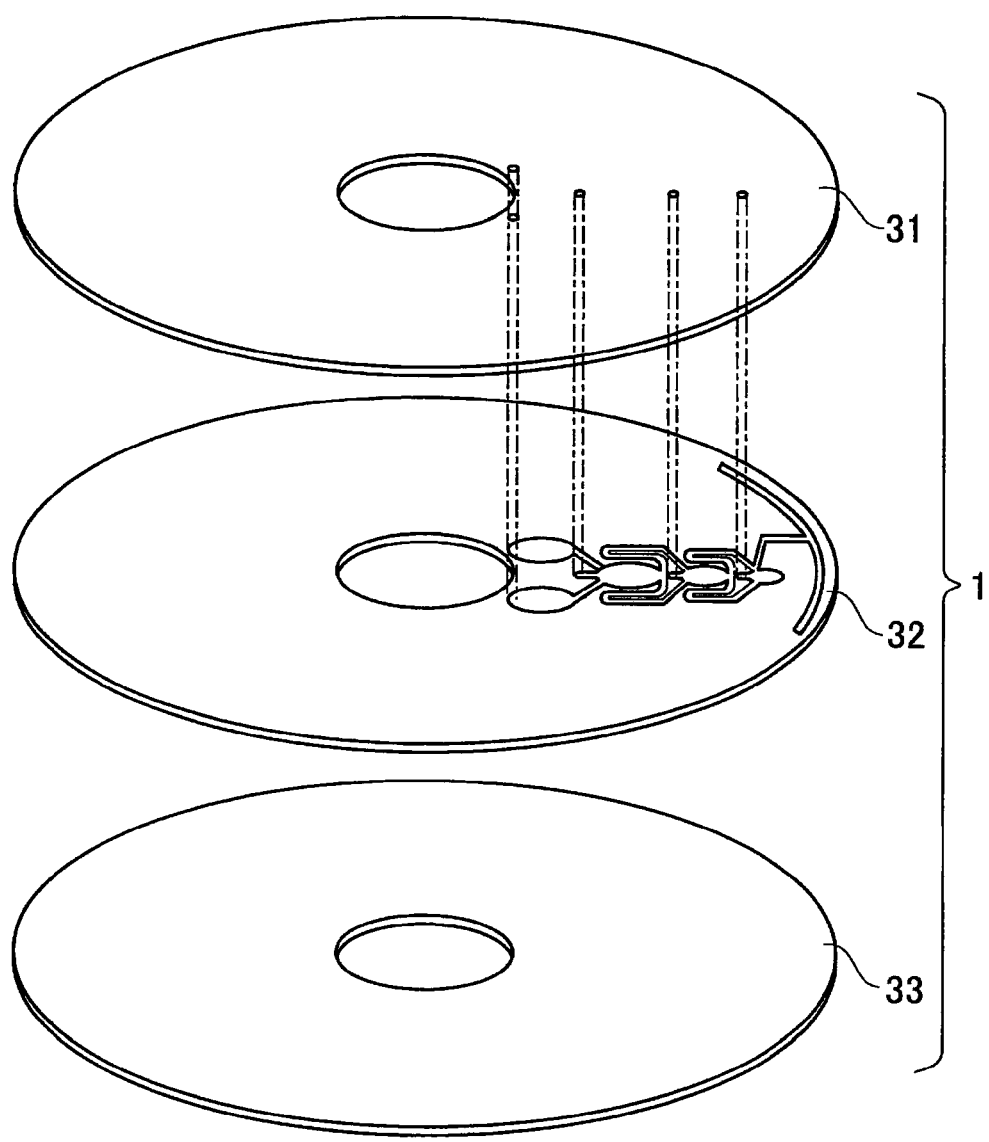
FIG. 3 is an exploded perspective view showing the liquid homogenizer shown in FIG. 1.

FIGS. 1 to 3 are schematic views showing the liquid homogenizer according to the first example of the present invention.

As shown in FIG. 1, the liquid homogenizer according to this example comprises a rotator 1 having a center hole formed therein, and having a disc shape having a predetermined rotation axis (not shown), the rotator 1 rotating around the rotation axis. The center hole and the rotation axis of the rotator 1 are in coaxial relationship with each other.

As shown in FIG. 2, the rotator 1 has a first base substrate 31 as a cover member of the rotator 1, a second base substrate 32 having an air space formed therein, and a third base substrate 33 as a basal member of the rotator 1, these base substrates 31 to 33 being mounted in the order the same as the above described order.

The first base substrate 31 has a specimen inlet port 16 and air openings 5, 9 and 13 formed therein. The air space in the second base substrate 32 is formed with a predetermined shape. The chambers and the channels are formed based on this air space with the first base substrate 31 and the third base substrate 33 being mounted on the second base substrate 32.

In this example, the rotator 1 has two specimen chambers 2 and 3, a first liquid-mixing chamber 6, a second liquid-mixing chamber 10, a third liquid-mixing chamber 14, and an overflow chamber 15 formed therein arranged in the direction from the rotation axis of the rotator 1 to the circumference (hereinafter simply referred to as an outward direction or an outer side) in the above-mentioned order. As shown in FIG. 1, the first liquid-mixing chamber 6, the second liquid-mixing chamber 10, and the third liquid-mixing chamber 14 are formed to be different from each other in distance from the rotation axis of the rotator 1. The liquid-mixing chambers 6, 10 and 14 have respective volumes such that the volume is getting smaller as the position of the liquid-mixing chamber is outer. That is to say, the third liquid-mixing chamber 14 has a volume smaller than that of the second liquid-mixing chamber 10, and the second mixing chamber 10 has a volume smaller than that of the first liquid-mixing chamber 6.

The rotator 1 additionally has a pair of straight channels 4 formed therein to respectively communicate two specimen chambers 2 and 3 with the first liquid-mixing chamber 6.

The rotator 1 additionally has a pair of channels 8 formed therein to communicate the first liquid-mixing chamber 6 with the second liquid-mixing chamber 10. The channels to communicate the liquid-mixing chambers are formed with inverted U-shape part. In this case, it is important that the apex of the inverted U-shape part is positioned in the direction closer to the rotation axis of the rotator 1 (hereinafter simply referred to as an inward direction or an inner side) compared to a connection port, the connection port being formed on the liquid-mixing chamber, and the liquid from the channel is injected to the liquid-mixing chamber through the connection port. To be more precise, the channels 8 are respectively extended, from the connection ports formed on outer side surface of the first liquid-mixing chamber 6, toward the inward direction, and extended with a U-shape turn to the outward direction at the folded part 7, and extended to the connection ports formed on the second liquid-mixing chamber 10. In the same way, the rotator 1 has a pair of channels 12 formed therein to communicate the second liquid-mixing chamber 10 with the third liquid-mixing chamber 14. The channels 12 are respectively extended, from the connection ports formed on outer side surface of the second liquid-mixing chamber 10, toward the inward direction, and extended with a U-shape turn to the outward direction at the folded part 11, and extended to the connection ports formed on the third liquid-mixing chamber 14. The third liquid-mixing chamber 14 and the overflow chamber 15 are communicated with each other through a channel. These chambers and channels collectively constitute a liquid-mixing unit. The liquid homogenizer according to the embodiment of this invention is preferred to have two or more liquid-mixing units.

Figure 8:
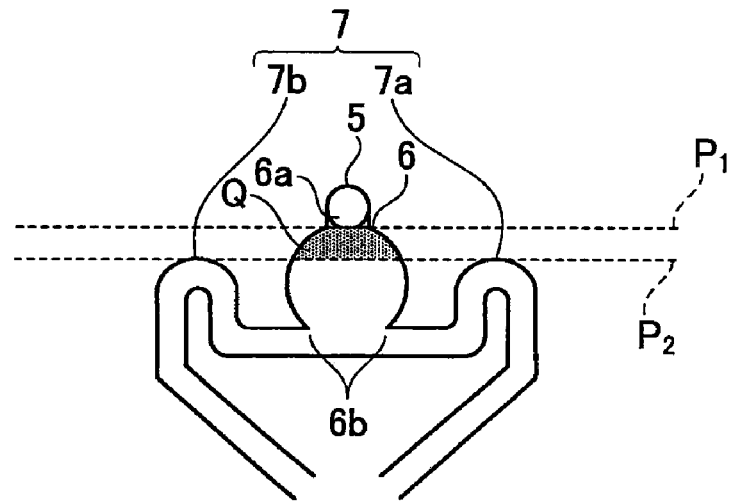
FIG. 8 is a schematic view explaining the position of the folded part, where
Figure 8:
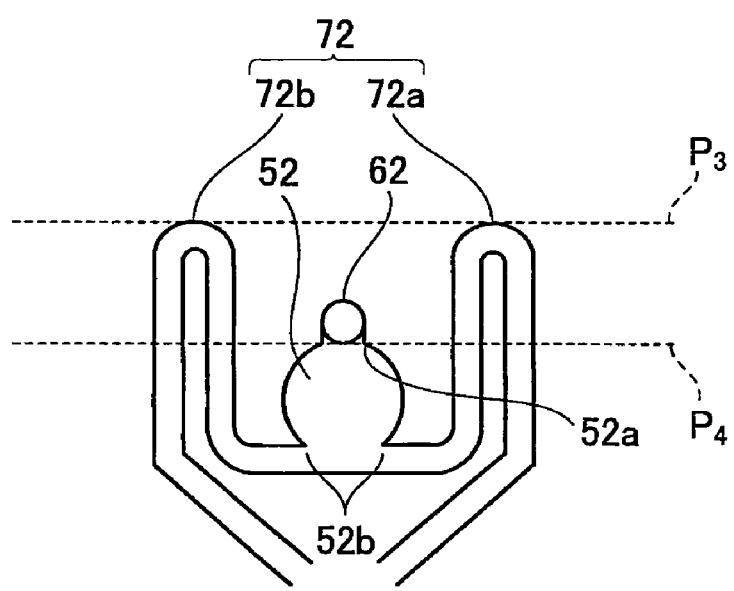

Referring now to FIG. 8, there is shown a positional relationship between the folded part and the liquid-mixing chamber. FIG. 8(a) shows the positional relationship between the first liquid-mixing chamber 6 and the folded part 7.

As shown in FIG. 8(a), two channels are extended from emission ports 6b formed on the first liquid-mixing chamber 6 to the second liquid-mixing chamber 10 which is not shown in FIG. 8(a), to have the first liquid-mixing chamber 6 communicate with the second liquid-mixing chamber 10. The channels have respective folded parts 7a and 7b formed to be inner side compared to the emission ports 6b of the first liquid-mixing chamber 6, the channels extended from the first liquid-mixing chamber 6. This constitution makes it possible for the liquid homogenizer according to this example to temporarily hold liquids in the proximity of the first liquid-mixing chamber 6 and the folded parts 7a and 7b under the condition that the rotator is rotating. This leads to the fact that the turbulent flow is certainly generated when the liquids are injected to the second liquid-mixing chamber 10 through the channels. In this example, the folded parts 7 are positioned at the outer side compared to the surface P1 (that is, "the inner surface positioned most inward" or "the surface closest to the rotation axis"), where the surface P1 is defined by points, collectively, including the point 6a which is positioned on the side surface positioned most inward of the first liquid-mixing chamber 6, the points being equal in distance with each other from the rotation axis. This constitution makes it possible for the liquid homogenize according to this example to achieve the sequential shift of the liquid from the first liquid-mixing chamber 6 to the second liquid-mixing chamber 10 with one rotation operation.

The first liquid-mixing chamber 6 is adapted to communicated with the air opening 5, which leads to the fact that the liquid flow could be interrupted by the air partly remaining in the first liquid-mixing chamber 6 after the air being injected through the air opening 5, when the liquid is shifted. In order to avoid this interruption, the folded parts 7 are required to be formed away from the rotation axis with a predetermined distance. This predetermined distance is preferred to be set such that the inner liquid-mixing chamber has a partial space having a volume Q substantially larger than the volume of the air injected through the air opening while the rotator is rotating, the partial space defined by the side surface positioned most inward P1 and a surface P2 having a distance, from the rotation axis, equal to the distance between the rotation axis and the folded parts 7, the surface P2 containing the apexes of the folded parts 7a and 7b. The volume of the air injected through the air opening while the rotator is rotating can be calculated in accordance with the conditions of the air opening, the conditions exemplified by a shape and a size. The volume Q of the partial space of the first liquid-mixing chamber 6 defined by the side surface P1 positioned most inward and the surface P2 having a distance, from the rotation axis, equal to the distance between the rotation axis and the folded part 7 may be set so that the first liquid-mixing chamber 6 can retain the liquid without the flow of the liquid being interrupted by the air which is injected in the first liquid-mixing chamber 6 while the rotator is rotating. In a precise sense, it is preferable that the volume Q be set according to the characteristics of the liquid. For example, the volume can be slightly smaller than the volume of the injected air when the liquid with high viscosity and high affinity for the air is used.

In addition, the folded parts 7a and 7b of respective channels, the channels extended from the first liquid-mixing chamber 6, are formed to be equal in distances with each other from the rotation axis, ensuring that the liquid is sequentially shifted between the liquid-mixing chambers by one rotation operation. This makes it possible for the liquid homogenizer according to this example to inject the divided liquids, the liquids divided by two or more channels, in the second liquid-mixing chamber 10 with the same timing after the divided liquids passing through the respective folded parts 7a and 7b with the same timing. The positional relationship between the second liquid-mixing chamber 10 and the folded parts 11 is equal to the positional relationship between the first liquid-mixing chamber 6 and the folded parts 7. Therefore, the description about the same positional relationship will be omitted to avoid tedious repetition. In this example, positions of the connection ports, i.e., the inlet ports and the emission ports, to have channels extended to and from the liquid-mixing chambers are not limited. However, it is preferable that the relative position of the inlet port and the emission port is set so that the inlet port is positioned inner compared to the emission port for each liquid-mixing chamber.

The manufacturing process of the liquid homogenizer will now be described hereinafter with reference to sectional views shown in FIGS. 4 and 5. The constitutional elements of the present example shown in FIGS. 4 and 5 the same as those shown in FIGS. 1 to 3 have respective reference numerals the same as those shown in FIGS. 1 to 3.

Figure 4:
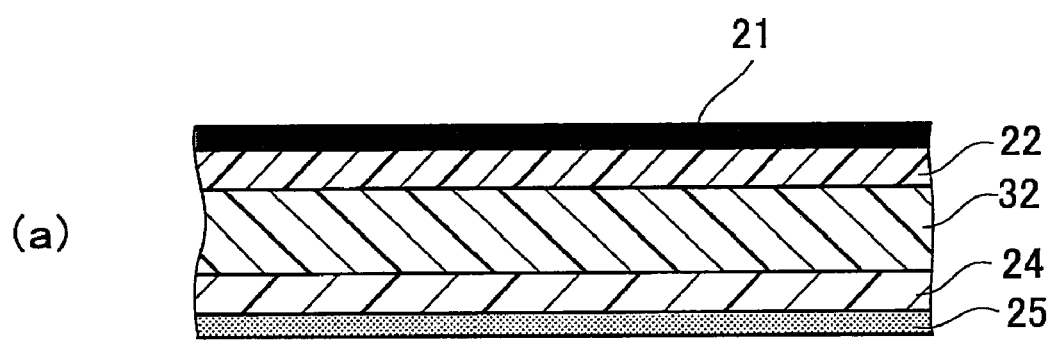
FIG. 4 is a sectional view showing one example of the manufacturing process of the liquid homogenizer shown in FIG. 1, where
Figure 4:
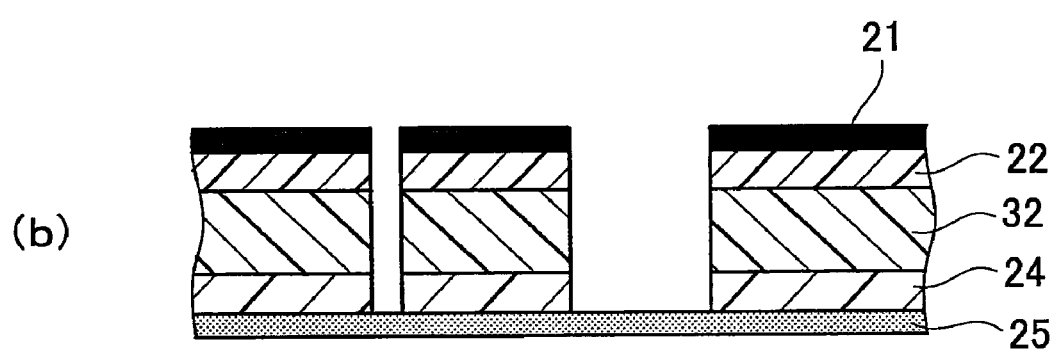

Firstly, as shown in FIG. 4, a layered member is prepared, the layered member being constituted by a release paper 21, an adhesive layer 22, a second base substrate 32, an adhesive layer 24, and a release paper 25 (see FIG. 4(a)). The release paper 21, the adhesive layer 22, the second base substrate 32, the adhesive layer 24, and the release paper 25 are then cut off, without the release paper 25 being cut off, by a cutting machine so that a predetermined air space is formed (see FIG. 4(b)), the cutting machine exemplified by a cutting plotter. The chambers and channels will be formed in the following steps based on this predetermined air space.

The release paper 21 is then removed from the layered member where the air space is formed, and the first base substrate (a cover member) 31 is then mounted on the adhesive layer 22. The air opening 5 and the specimen inlet port 16 may originally be formed in the first base substrate 31. Alternatively, the air opening 5 and the specimen inlet port 16 may be formed in the first base substrate 31 after the first base substrate 31 is mounted on the layered member.

Figure 5:
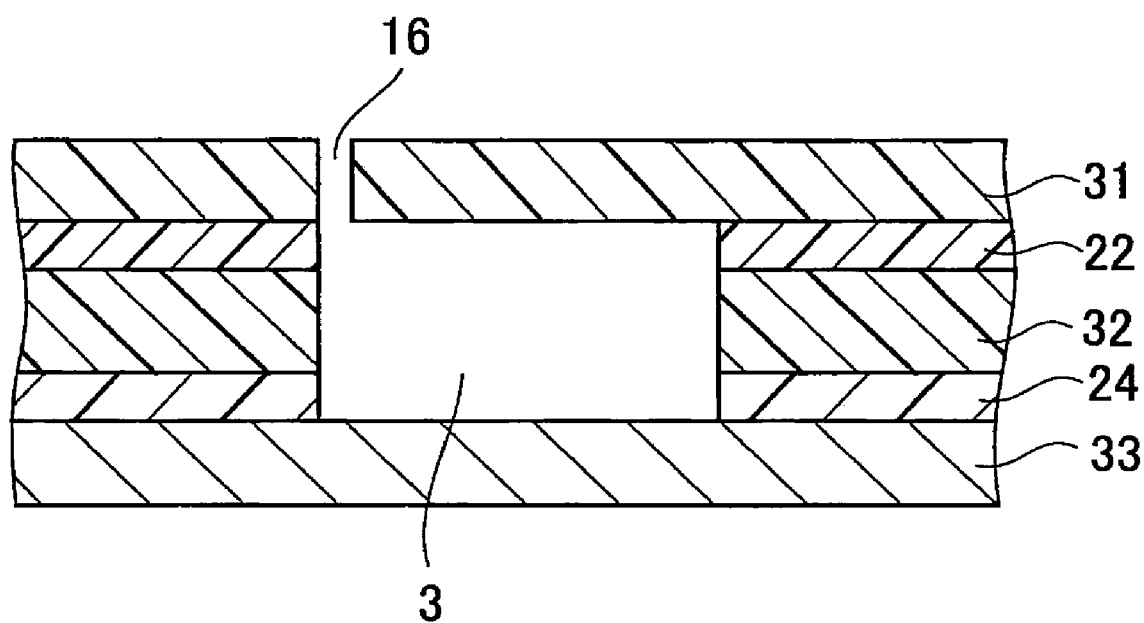
FIG. 5 is a sectional view showing the liquid homogenizer shown in FIG. 1.

The release paper 25 is then removed from the layered member, and the third base substrate (basal member) 33 is then mounted on the adhesive layer 24 so that the liquid homogenizer is constructed as shown in FIG. 5.

Here, the second base substrate 32 is constituted by a two-sided adhesive sheet (core layer (the second base substrate 32) having a thickness of 50 μm, adhesive layers 22 and 24 on respective sides of the core layer having a thickness of 25 μm by FLEXCON). The adhesive layer 24 is processed with an ethanol solution containing 10% of Triton-100 so that the hydrophilicity at the chambers and the channels are increased. Here, the process of incising the second base substrate 32 is conducted with the cutting plotter (CE3000-40 by GRAPHTEC).

The method of liquid homogenization using the above-mentioned liquid homogenizer will now be described hereinafter.

Firstly, a liquid specimen and a liquid reagent (or a diluted solvent) are separately injected from the respective two specimen inlet ports 16 to the respective two specimen chambers 2 and 3. The liquid homogenizer is then set to a rotation device manufactured for this liquid homogenizer. The liquid homogenizer is then rotated to generate the centrifugal force. The liquid specimen and the liquid reagent are then injected, by the centrifugal force, in the first liquid-mixing chamber 6 through the respective channels 4, where the liquid specimen and the liquid reagent are collided with each other, which causes a turbulent flow with the result that the liquid specimen and the liquid reagent are agitated to be mixed. The mixed liquid specimen and the liquid reagent are then injected to the second liquid-mixing chamber 10 from the first liquid-mixing chamber 6 through the two channels 8, which causes a turbulent flow in this second liquid-mixing chamber 10 with the result that the liquid specimen and the liquid reagent are again agitated to be mixed. The mixed liquid specimen and the liquid reagent are then injected to the third liquid-mixing chamber 14 from the second liquid-mixing chamber 10 through the two channels 12, which causes a turbulent flow in this third liquid-mixing chamber 14 with the result that the liquid specimen and the liquid reagent are again agitated to be mixed. The liquid homogenizer, thus, makes it possible to mix the liquids more evenly due to the fact that the mixing process is carried out three times. The liquid specimen overflowed from the third liquid-mixing chamber 14 is shifted to the overflow chamber 15 through the channel.

As described in the above, the liquid homogenizer according to this example can evenly mix the liquid with only one rotation operation of the rotator due to the fact that the volumes of the chambers are set to be smaller as the chambers are positioned outer, with the chambers being communicated with each other through two or more channels having respective inverted U-shape parts.

COMPARATIVE EXAMPLE

Figure 9:
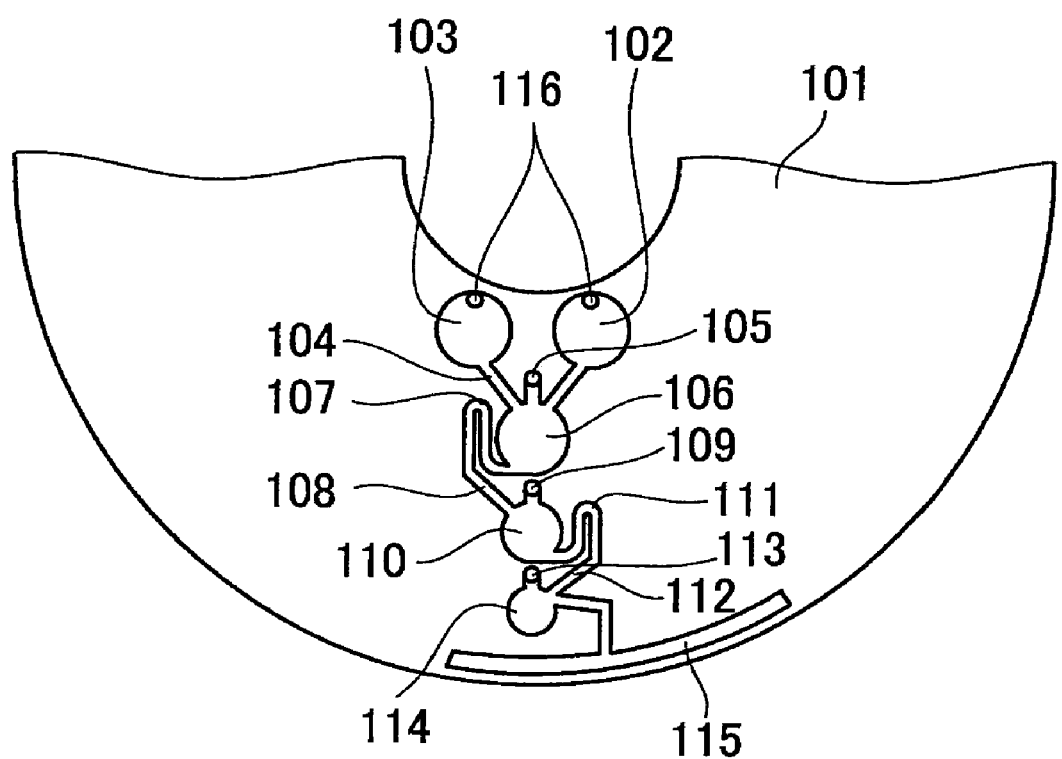
FIG. 9 is a plan view showing one comparative example of the liquid homogenizer.

The liquid homogenizer according to the comparative example is manufactured in a similar manner with the liquid homogenizer according to the first example, having a similar construction with the liquid homogenizer according to the first example except that the chambers and channels are formed to have shapes as shown in FIG. 9, instead of the shapes as shown in FIG. 1.

As shown in FIG. 9, the rotator 101 has two specimen chambers 102 and 103, a first liquid-mixing chamber 106, a second liquid-mixing chamber 110, a third liquid-mixing chamber 114, and an overflow chamber 115 formed therein arranged in this described order in the outward direction. These chambers are communicated with each other through one channel.

The rotator 101 further has two straight channels 104 to ensure that the two specimen chambers 102 and 103 communicate with the first liquid-mixing chamber 106, a channel 108 to ensure that the first liquid-mixing chamber 106 and the second liquid-mixing chamber 110 communicate with each other, and a channel 112 to ensure that the second liquid-mixing chamber 110 and the third liquid-mixing chamber 114 communicate with each other. The first liquid-mixing chamber 106, the second liquid-mixing chamber 110, and the third liquid-mixing chamber 114 respectively have air openings 105, 109, and 112 formed thereon. The channels, ensuring that the liquid-mixing chambers communicate with each other, have respective folded parts 107 and 112 having an inverted U-shape, the apex of the inverted U-shape part being closer to the rotation axis of the rotator 101 (that is, an inward direction or a inner side) compared to a connection port of the liquid-mixing chamber where the channel is extended thereto and where the liquid is injected therethrough.

To be more precise, the two specimen chambers 102 and 103 are communicated with the first liquid-mixing chamber 106 respectively through the pair of straight channels 104. The channel 108 is extended, from the connection port formed on outer side of the first liquid-mixing chamber 6, toward the inward direction, and extended with a U-shape turn to the outward direction at the folded part 107, and extended to the connection port formed on the second liquid-mixing chamber 110. In the same way, the channel 112 is extended, from the connection port formed on outer side of the second liquid-mixing chamber 110, toward the inward direction, and extended with a U-shape turn to the outward direction at the folded part 111, and extended to the connection port formed on the third liquid-mixing chamber 114. The third liquid-mixing chamber 114 and the overflow chamber 115 are communicated with each other through a channel.

Figure 10:
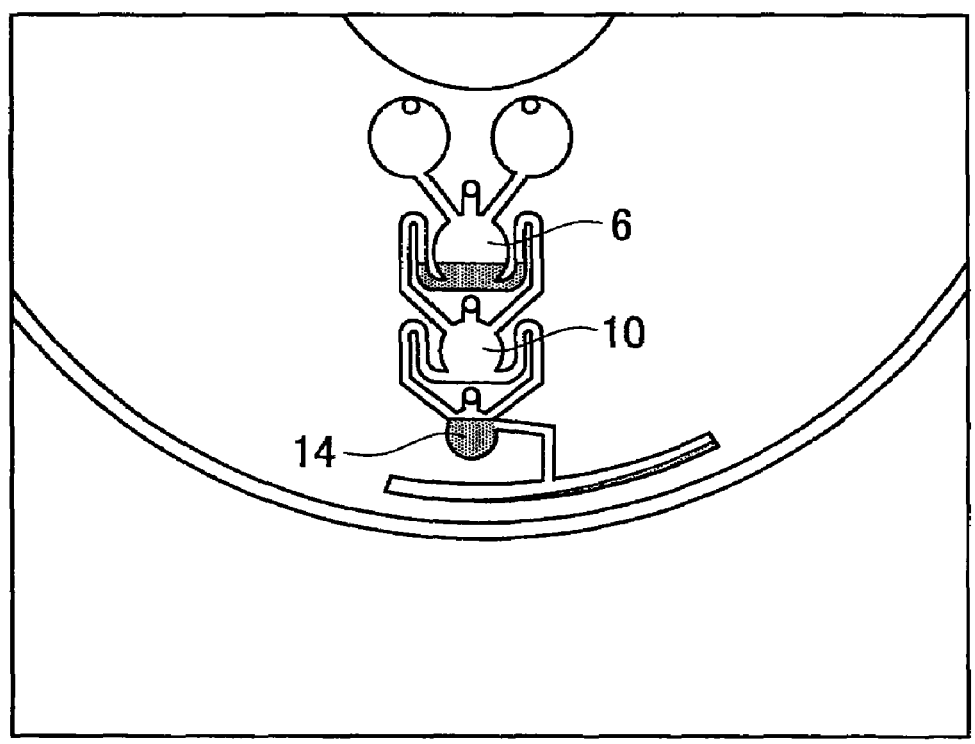
FIG. 10 is a schematic view showing the result of the evaluation using the liquid homogenizer according to the first example shown in FIG. 1, where
Figure 10:
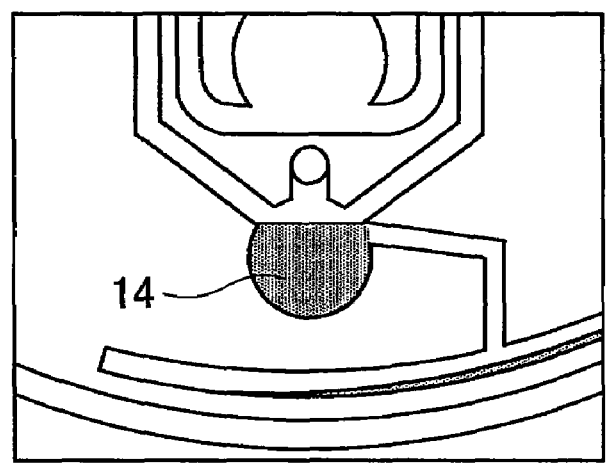
Figure 11:
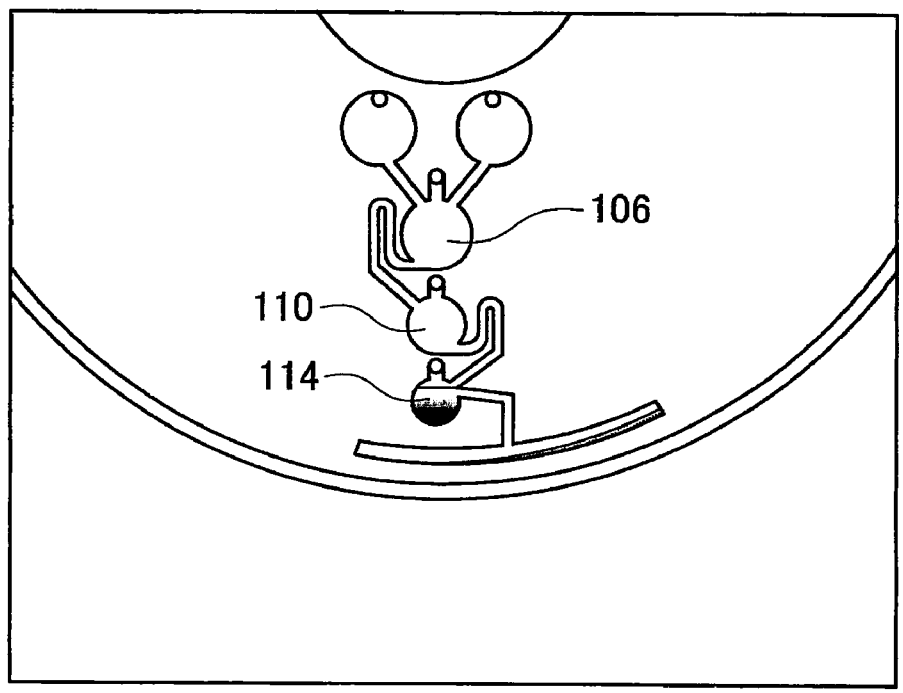
FIG. 11 is a schematic view showing the result of the evaluation using the liquid homogenize according to one comparative example shown in FIG. 9, where
Figure 11:
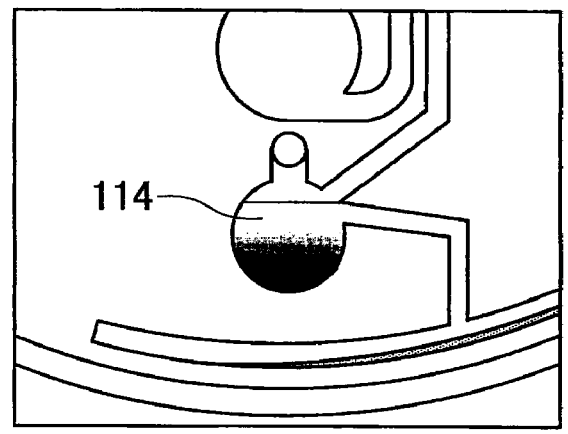
Figure 12:
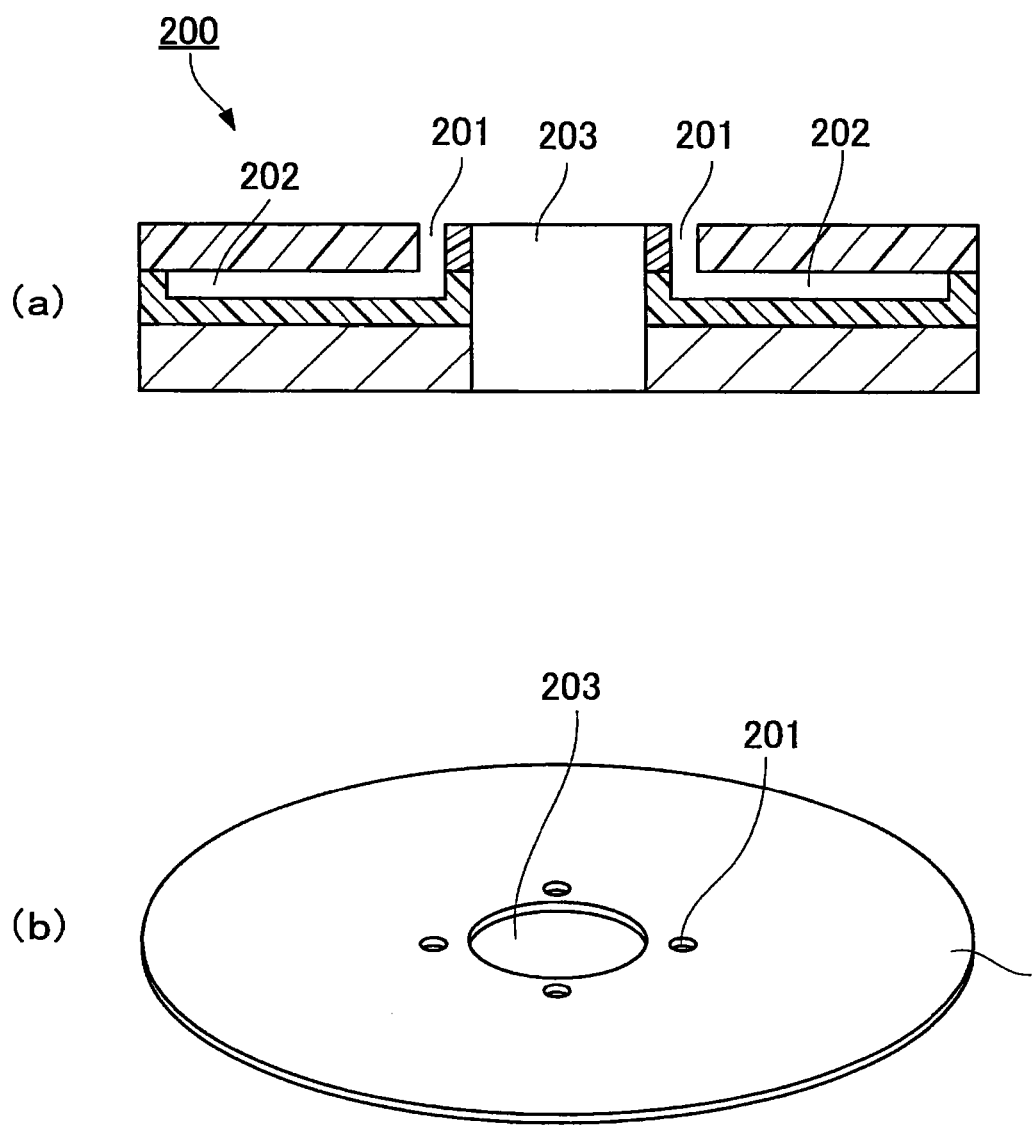
FIG. 12 is a schematic view showing the rotation device according to the prior art, where

The mixing degree using the liquid homogenizers according to the first example and the comparative example manufactured as above described was evaluated with red-colored latex particles in the form of a suspension (having a diameter of 0.313 μm by SEKISUI). The suspension of the red-colored latex particles and water were injected through the two respective specimen inlet ports, and the rotator was rotated for 1 minute with the rotation velocity of 1600 rpm so that the suspension of the red-colored latex particles and water were mixed. FIG. 10(a) is an overall view of the liquid homogenizer showing the result of the evaluation according to the first example, and FIG. 10(b) is a partial enlarged view of FIG. 10(a). FIG. 11(a) is an overall view of the liquid homogenizer showing the result of the evaluation according to the comparative example, and FIG. 11(b) is a partial enlarged view of FIG. 11(a). As shown in FIG. 10(a), the liquid injected to the first liquid-mixing chamber 6 was shifted to the third liquid-mixing chamber 14 through the second liquid-mixing chamber 10. As shown in FIG. 10(b), the suspension of the red-colored latex particles and water were evenly mixed under the condition that the liquid homogenizer according to the first example was used. On the other hand, the suspension of the red-colored latex particles and water were not evenly mixed, and the suspension of the red-colored latex particles was precipitated downward under the condition that the liquid homogenizer according to the comparative example was used as shown in FIG. 11(b).

These results show that the liquid homogenizer according to the first example can mix the suspension of the red-colored latex particles and water more evenly than the liquid homogenizer according to the comparative example without extending the space where the channels are formed. These results were then quantified with the measurement of the absorbance at a maximum absorption wavelength using an optical fiber type spectroscope. The measurement showed that the mixed liquid had the same absorbance at any measured positions under the condition that the liquid homogenizer according to the first example was used, while the mixed liquid had the absorbance with unevenness with respect to the measured positions under the condition that the liquid homogenizer according to the comparative example was used.

As will be seen from the above detailed description, the liquid homogenizer according to this example has a rotator 1 rotating around a predetermined rotation axis, and a plurality of liquid-mixing chambers 6, 10, and 14 for mixing a plurality of liquids and formed in the rotator 1 with different distances from the rotation axis with each other, and a plurality of channels 8 and 12 respectively extending from and held in fluid communication with the liquid-mixing chambers 6, 10 and 14, where the liquid-mixing chambers next to each other are communicated through two or more channels. Therefore, the liquid homogenizer can evenly mix the liquids with smaller space compared to the conventional liquid homogenizer, resulting from the fact that the liquids are shifted, by the centrifugal force generated by the rotation of the rotator 1, from the liquid-mixing chamber formed on the close side with respect to the rotation axis to the liquid-mixing chamber formed on the far side with respect to the rotation axis through the plurality of channels, where the injected liquids are collided with each other while causing a turbulent flow.

While there has been described about the fact that the folded part having an inverted U-shape is positioned outer side compared to the side surface positioned most inward of the inner liquid-mixing chamber where the channel is extended therefrom, the folded part having an inverted U-shape may be positioned inner side compared to the side surface positioned most inward of the inner liquid-mixing chamber where the channel is extended therefrom, which can have a same advantageous effect. This constitution will now be described hereinafter as a second example.

SECOND EXAMPLE

Figure 6:
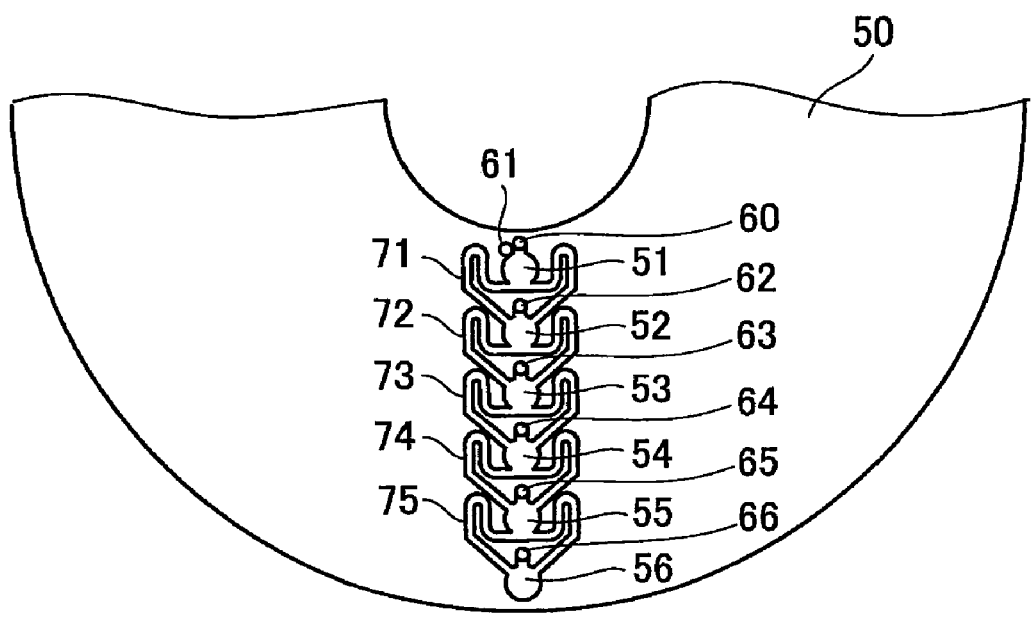
FIG. 6 is a plan view showing the liquid homogenizer according to the second example of the present invention.
Figure 7:
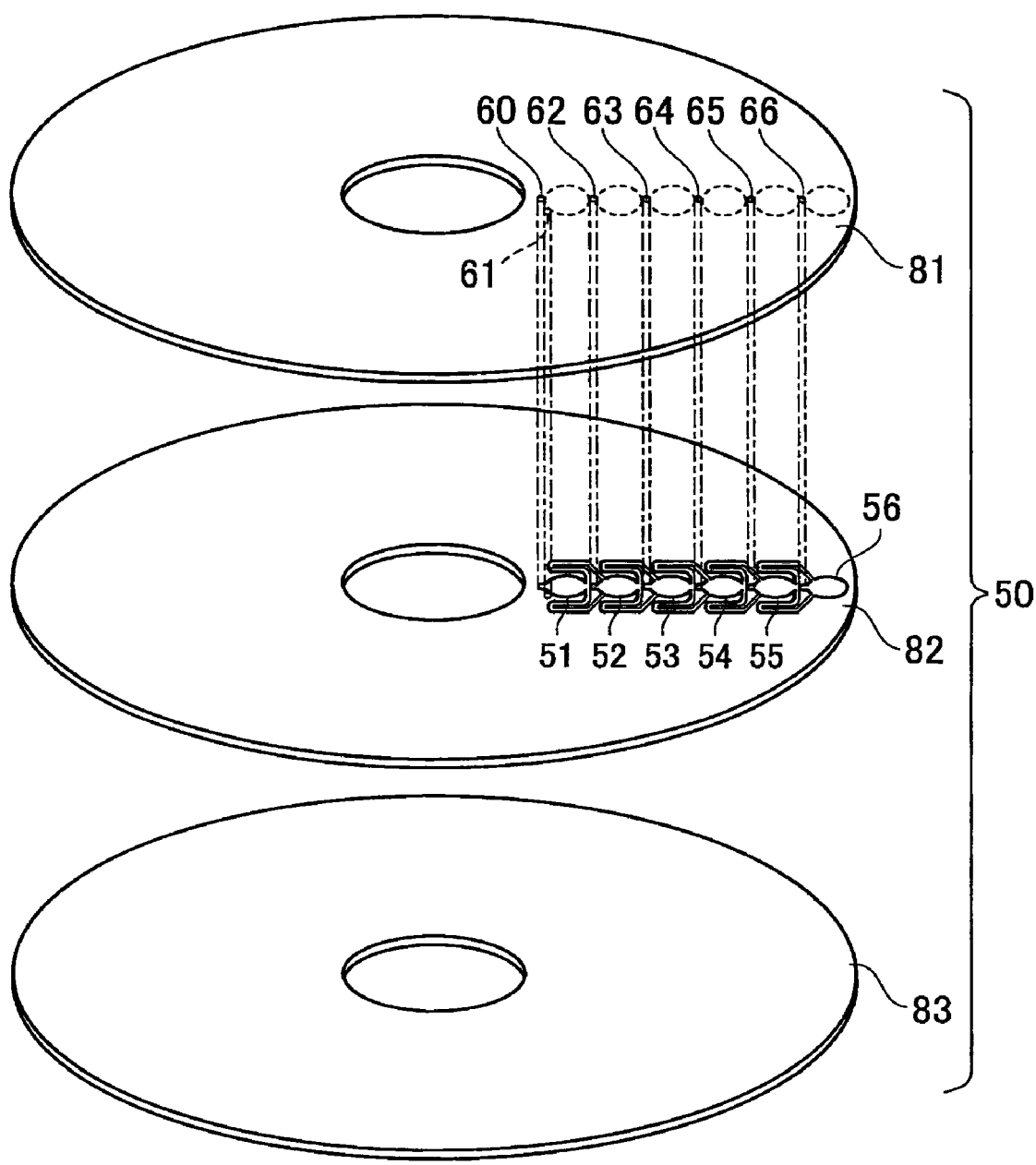
FIG. 7 is an exploded plan view showing the liquid homogenizer shown in FIG. 6, where

FIGS. 6 and 7 are schematic views showing an analyzer employing a liquid homogenizer according to the second example.

The liquid homogenizer employed by the analyzer according to this example is constituted, in a similar manner with the liquid homogenizer according to the first example, by a rotator 50 having a center hole formed therein, and having a disc shape having a predetermined rotation axis (not shown), the rotator 50 rotating around the rotation axis, as shown in FIG. 6. The center hole and the rotation axis of the rotator 50 are in coaxial relationship with each other.

As shown in FIG. 7, the rotator 50 has a first base substrate 81 as a cover member of the rotator 50, a second base substrate 82 having an air space formed therein, and a third base substrate 83 as a basal member of the rotator 50, these base substrates 81 to 83 being mounted in the order the same as the above described order.

The first base substrate 81 has a specimen inlet port 60 and air openings 61 to 66 formed therein. The first base substrate 81 further has a plurality of recess portions having a predetermined shape respectively positioned between the specimen inlet port 60 and the air openings 61 to 66. The air space formed in the second base substrate 82 has a predetermined shape corresponding to the shapes formed in the first base substrate 81. The chambers and the channels are formed by the air space under the condition that the first base substrate 81 and the third base substrate 83 are mounted on the second base substrate 82.

In this example, the rotator 50 has a first chamber 51, a second chamber 52, a third chamber 53, a fourth chamber 54, a fifth chamber 55, and a sixth chamber 56 formed therein arranged in the direction from the center hole to the outer side. As shown in FIG. 6, the first chamber 51, the second chamber 52, the third chamber 53, the fourth chamber 54, the fifth chamber 55, and the sixth chamber 56 are formed with the respective distances from the center hole, that is, the rotation axis of the rotator 50, the distances being different from each other.

The rotator 50 further has a couple of channels 71 formed therein having an inverted U-shape to have the first chamber 51 and the second chamber 52 communicated therethrough. In a similar manner, the rotator 50 has a couple of channels 72 formed therein having an inverted U-shape to have the second chamber 52 and the third chamber 53 communicated therethrough, a couple of channels 73 formed therein having an inverted U-shape to have the third chamber 53 and the fourth chamber 54 communicated therethrough, a couple of channels 74 formed therein having an inverted U-shape to have the fourth chamber 54 and the fifth chamber 55 communicated therethrough, a couple of channels 75 formed therein having an inverted U-shape to have the fifth chamber 55 and the sixth chamber 56 communicated therethrough. The second to sixth chambers 52 to 56 have respective air openings 62 to 66 formed thereon.

In this example, each of the channels is designed so that the folded part is positioned inner side compared to the side surface positioned most inward of the inner liquid-mixing chamber, where the channel is extended from the inner liquid-mixing chamber to the outer liquid-mixing chamber. This leads to the fact that the liquid is shifted and then mixed with the rotator 50 being rotated and halted repetitively.

The liquid homogenizer according to this example has the same construction with the liquid homogenizer according to the first example except for the above mentioned constitutional elements. The manufacturing process of the rotator according to this example is the same as the manufacturing process according to the first example.

Referring now to FIG. 8, there is shown a positional relationship between the folded part and the liquid-mixing chamber. FIG. 8(*b*) shows the positional relationship between the second liquid-mixing chamber 52 and the folded part 72.

As shown in FIG. 8(*b*), two channels are extended from emission ports 52*b* formed on the second liquid-mixing chamber 52 to the third liquid-mixing chamber 53 which is not shown in FIG. 8(*b*), to have the second liquid-mixing chamber 52 communicate with the third liquid-mixing chamber 53. The channels, extending from the second liquid-mixing chamber 52 positioning inner side, have respective folded parts 72*a* and 72*b*, the folded parts 72*a* and 72*b* positioned inner side compared to the emission ports 52*b* of the second liquid-mixing chamber 52. This constitution makes it possible for the liquid homogenizer according to this example to temporarily hold the liquids in the proximity of the second liquid-mixing chamber 52 and the folded parts 72 under the condition that the rotator is rotating. This leads to the fact that the turbulent flow is certainly generated when the liquid is injected to the third liquid-mixing chamber 53, positioned outer side, through the channels. In this example, the folded parts 72 are positioned at the inner side compared to the surface P4 (that is, "the side surface positioned most inward" or "the surface closest to the rotation axis"), where the surface P4 is defined by points, including the point 52*a* which is positioned most inward of the second liquid-mixing chamber 52, the points having distances from the rotation axis equal with each other. This constitution makes it possible for the liquid homogenizer according to this example to have the liquid shifted between the liquid-mixing chambers to be mixed, with the rotator being rotated and halted repetitively.

While there has been described about the fact that the folded parts 72a and 72b of the channels extended from the second liquid-mixing chamber 52 are placed on the same imaginary surface P3, the folded parts 72a and 72b may not be placed on the imaginary surface P3, where the imaginary surface P3 is constituted by points having the distances equal to each other from the rotation axis. In this example, it is unnecessary for the liquids to be injected in the liquid-mixing chamber with the same timing through the plurality of the channels, resulting from the fact that the rotator is repetitively rotated and halted. Rather, the collisions are effectively caused in the case that the timing for injecting the liquids from the respective channels is not synchronized with each other, ensuring that the turbulent flow is certainly caused, and that the liquids are evenly mixed more easily. Therefore, the folded parts 72a and 72b are not required to be placed on the imaginary surface P3 where the points on the imaginary surface P3 have the distances equal to each other from the rotation axis. Rather, it is preferable that the folded parts 72a and 72b are not placed on the imaginary surface P3. This constitution makes it possible to intentionally inject the liquids with the timing different from each other, which results in the fact that the turbulent flow is certainly caused. The positional relationship between the first liquid-mixing chamber 51 and the channels 71, the third liquid-mixing chamber 53 and the channels 73, the fourth liquid-mixing chamber 54 and the channels 74, and the fifth liquid-mixing chamber 55 and the channels 75 are the same as the positional relationship between the second liquid-mixing chamber 52 and the channels 72. Therefore, the description about the same positional relationship will be omitted to avoid tedious repetition.

Here, an anti-human albumin polyclonal antibody labeled with latex was held in the second chamber 52 in a freeze-dry condition, and the first base substrate 81 was mounted on the second base substrate 82. The labeling with latex was conducted by having the rabbit anti-human albumin polyclonal antibody, which is adapted to react with an albumin, adsorbed with latex particles (having a diameter of 160 μm) with the physical adsorption by well known methods.

The method of measuring a liquid mixing using the liquid homogenizer will now be described hereinafter by giving an example of measuring albumin based on the antigen-antibody reaction. In this measurement example, the process of mixing and antigen-antibody reaction was firstly conducted in the liquid homogenizer. The process of measuring an absorbance was then conducted using an optical fiber. In this liquid homogenizer, the first chamber 51 was used to have a sample injected therein. The second chamber 52 was used to have an antibody held in a dry condition, the antibody being adapted to react with the albumin, and was used to have the antibody melted under the condition that the sample was injected therein. The third chamber 53, the fourth chamber 54, and the fifth chamber 55 were used to have the sample mixed and reacted therein. The sixth chamber 56 was used to have the mixed and reacted liquid to be measured by the optical fiber.

The operating step will be described hereinafter. Firstly, the sample (PBS buffer fluid containing an albumin) was injected to the first chamber 51 through the specimen inlet port 60. The sample was then shifted by capillary force to the position short of the second chamber 52 through the channels 71 having an inverted U-shape. The rotator was then rotated to have the sample injected to the second chamber 52. At the same time, the antibody held in a dry condition was melted to react with the sample. The rotator was then halted to stop the rotation, where the mixed and reacted liquid was shifted by capillary force to the position short of the third chamber 53. The rotator was then repetitively rotated and halted to ensure that the mixed and reacted liquid was shifted to the fifth chamber 55 through the third chamber 53 and the fourth chamber 54, and the liquids was mixed in each chamber. The mixed and reacted liquid was finally shifted to the sixth chamber 56, where the mixed and reacted liquid, that is, a sample liquid, was optically measured with the optical fiber. According to the time-course measurement, the absorbance was increased with respect to the course of time, which represents that the reaction was proceeding.

As will be seen from the above detailed description, the liquid homogenizer employed by the analyzer according to this example has a rotator 50 rotating around a predetermined rotation axis, and two or more liquid-mixing chambers 51 to 56 for mixing two or more liquids and formed in the rotator 1 with different distances from the rotation axis with each other, and two or more channels 71 to 75 respectively extending from and held in fluid communication with the liquid-mixing chambers 51 to 56, where each of the liquid-mixing chambers is communicated through two or more channels, and the liquids are shifted, by the centrifugal force generated by the rotation of the rotator 1, from the liquid-mixing chamber formed on the close side with respect to the rotation axis to the liquid-mixing chamber formed on the far side with respect to the rotation axis through the plurality of channels, where the injected liquids are collided with each other while causing a turbulent flow, which results in the liquids to be evenly mixed. Therefore, it is not necessary for the liquid homogenizer to have channels formed to be winding and to have a large space to have the winding channels formed therein due to the fact that the liquids are not necessary to be mixed in the channels. The analyzer thus constructed can evenly and efficiently mix the liquids with small space, and that the measurement can be conducted with high repeatability, by means of electrochemical or optical method for detecting reaction or amount of physical or chemical change caused by the reaction.

What is claimed is:

1. A liquid homogenizer for mixing two or more liquids, comprising a rotator rotatable around a rotation axis, said rotator having:

at least two liquid-mixing chambers different from each other in distance from said rotation axis;

two or more specimen chambers which said liquids are respectively injected to, said liquids from said specimen chambers being mixed in said liquid-mixing chambers; and at least two channels through which one of said liquid-mixing chambers is communicated with the other of said liquid-mixing chambers with each channel extending from an opposite side of the other of said liquid-mixing chambers with respect to a mirror axis, said mirror axis intersecting the centers of said liquid-mixing chambers and radially extending from the rotation axis, wherein said liquid-mixing chambers include an outer liquid-mixing chamber and an inner liquid-mixing chamber close to said rotation axis in comparison with said outer liquid-mixing chamber, wherein said channels and said liquid mixing chambers are symmetrical with respect to said mirror axis;

when said rotator is rotating around said rotation axis, said liquids are shifted by a centrifugal force to said outer liquid-mixing chamber from said inner liquid-mixing chamber through said channels, and agitated to be mixed by turbulent flows in said outer liquid-mixing chamber, said inner liquid-mixing chamber has emission ports formed with one ends of said channels, said outer liquid-mixing chamber has inlet ports to have said liquids injected therethrough formed with the other ends of said channels, said channels are respectively extended from said emission ports to said inlet ports, and said channels have folded parts being closer to said rotation axis than said emission ports of said inner liquid-mixing chamber.

2. A liquid homogenizer as set forth in claim 1, wherein said inner liquid-mixing chamber is defined by surfaces including a closest surface closest to said rotation axis of all said surfaces, and said folded parts of said channels extending from said inner liquid-mixing chamber are farther in comparison with said closest surface to said rotation axis.

3. A liquid homogenizer as set forth in claim 2, wherein said liquid-mixing chambers have air openings formed thereon, and said folded parts are formed away from said rotation axis with a predetermined distance, said predetermined distance being set so that said inner liquid-mixing chamber has a partial space having a volume substantially larger than air volume injected through said air openings when said rotator is rotating, said partial space being defined by said closest surface and another surface having a distance, from said rotation axis, equal to the distance between said rotation axis and said folded part.

4. A liquid homogenizer as set forth in claim 2, wherein said folded parts of said channels extended from each liquid-mixing chamber are formed to be equal in distances with each other from said rotation axis.

5. A liquid homogenizer as set forth in claim 4, wherein said inlet ports of said outer liquid-mixing chamber are formed to be different in distance from said rotation axis with each other.

6. A liquid homogenizer as set forth in claim 2, wherein said inner liquid-mixing chamber is larger in volume than that of said outer liquid-mixing chamber.

7. A liquid homogenizer as set forth in claim 1, wherein said inner liquid-mixing chamber is defined by surfaces including a closest surface closest to said rotation axis of all said surfaces, and said folded parts of said channels extended from said inner liquid-mixing chamber are formed to be closer in comparison with said closest surface to said rotation axis.

8. A liquid homogenizer as set forth in claim 7, wherein said folded parts of said channels extended from each liquid-mixing chamber are formed to be different in distance to said rotation axis.

9. A liquid homogenizer as set forth in claim 7, wherein said rotator is operated to be repetitively rotated and halted.

10. A liquid homogenizer as set forth in claim 1, wherein said inlet ports of said liquid-mixing chambers are formed to be upper in comparison with said emission ports in a thickness direction.

11. An analyzer for analyzing a liquid specimen, comprising: a rotator; and two or more chambers and channels formed in said rotator, wherein said liquid specimen is urged to be shifted to one of said chambers by a centrifugal force generated by a rotation of said rotator through said channels, the liquid specimen being analyzed in the chamber, and further comprising the liquid homogenizer as set forth in any one of claims 1 to 10 for mixing two or more liquids, wherein said rotator, said channels, and said liquid-mixing chambers are at least partly formed by the rotator, the channels, and the liquid-mixing chambers of said liquid homogenizer.

12. An analyzer as set forth in claim 11, wherein one of said liquid-mixing chambers is formed as a reaction chamber so that said liquid specimen and a reagent are reacted therein.

13. An analyzer as set forth in claim 12, wherein one of said liquid-mixing chambers is formed as a pretreatment chamber so that said liquid specimen is pretreated therein.

* * * * *